(12) United States Patent
Helfman et al.

(10) Patent No.: US 8,197,830 B2
(45) Date of Patent: Jun. 12, 2012

(54) DISSOLVABLE PADS FOR SOLUTION DELIVERY TO A SURFACE

(75) Inventors: Bradley David Helfman, Solon, OH (US); John H. Viscovitz, Akron, OH (US)

(73) Assignee: GOJO Industries, Inc., Akron, OH (US)

( * ) Notice: Subject to any disclaimer, the term of this patent is extended or adjusted under 35 U.S.C. 154(b) by 1459 days.

(21) Appl. No.: 11/037,977

(22) Filed: Jan. 18, 2005

(65) Prior Publication Data

US 2006/0159729 A1 Jul. 20, 2006

(51) Int. Cl.
*A61K 8/02* (2006.01)

(52) U.S. Cl. ........................................ 424/401

(58) Field of Classification Search .................. None
See application file for complete search history.

(56) References Cited

U.S. PATENT DOCUMENTS

| | | | | |
|---|---|---|---|---|
| 4,863,655 A | 9/1989 | Lacourse et al. | ................ | 264/53 |
| 5,382,285 A | 1/1995 | Morrison | ...................... | 106/122 |
| 5,895,780 A * | 4/1999 | Tokosh et al. | ................. | 510/145 |
| 6,054,204 A | 4/2000 | Lazarus | ......................... | 428/219 |
| 6,106,849 A | 8/2000 | Malkan et al. | ................ | 424/401 |
| 6,177,391 B1 | 1/2001 | Zafar | ............................. | 510/131 |
| 6,623,854 B2 * | 9/2003 | Bond | ............................. | 428/370 |
| 7,077,994 B2 * | 7/2006 | Bond et al. | ........................ | 422/1 |
| 2002/0098994 A1 | 7/2002 | Zafar | | |
| 2004/0048759 A1 | 3/2004 | Ribble et al. | ................... | 510/141 |
| 2004/0071755 A1 | 4/2004 | Fox | ................................. | 424/443 |
| 2004/0202632 A1 * | 10/2004 | Gott et al. | ................... | 424/70.13 |
| 2005/0087317 A1 * | 4/2005 | Rydell | ........................... | 162/158 |

FOREIGN PATENT DOCUMENTS

| | | |
|---|---|---|
| DE | 21 26 161 | 12/1971 |
| EP | 0 372 388 | 6/1990 |
| EP | 1 317 916 | 6/2003 |
| GB | 1 532 457 | 11/1978 |
| JP | 2008/215104 | 8/1996 |
| WO | WO 02/26896 | 4/2002 |

OTHER PUBLICATIONS

Brochure for FLO-PAK BIO 8 Loosefill, by FP International, dated Sep. 2003.
Article entitled Clean Green Packing by Starch Tech, Inc., retrieved online Apr. 15, 2005.

\* cited by examiner

*Primary Examiner* — Bethany Barham
(74) *Attorney, Agent, or Firm* — Renner Kenner Greive Bobak Taylor & Weber

(57) ABSTRACT

A dissolvable pad for delivery of a solution to a surface includes a water soluble substrate, and a solution retained in or on said water soluble substrate and available for use without activation by water. The water soluble substrate is soluble in water so as to be safely disposable into public water systems by exposing it to water after the solution therein has been desirably employed. Because the solution in the water soluble substrate is available for use without exposing the substrate to water, the substrate may function as an applicator, and, in some embodiments, as a scrubbing substrate as well.

12 Claims, No Drawings

DISSOLVABLE PADS FOR SOLUTION DELIVERY TO A SURFACE

BACKGROUND OF THE INVENTION

The present invention generally resides in the art of cleaning compounds and, more particularly, resides in the art of water soluble cleaning pads, wherein a cleaning compound is retained in a water-soluble substrate.

Pads and wipes are generally known and employed in the prior art, and typically include a substrate that retains a useful amount of a solution for delivery to a surface. The substrates are usually fabric-based substrates in which the solution is absorbed for use through rubbing the substrate onto a surface. The solutions deliverable in this manner include cleansing compounds, sanitizing compounds, bug repellant compounds, sun screen compounds, hard surface treatment compounds and the like. The pad or wipe is employed simply by rubbing it on the surface to be treated, for example, in the case of a wipe containing a personal cleansing compound, a body part.

In the prior art, a great many of these pads and wipes are thrown away after the useful solution therein has been exhausted, and this creates waste. Thus, particularly in the art of personal cleansing, some efforts have been made to provide a water soluble pad that retains a cleansing compound. But the known water soluble pads of this type retain cleansing compounds that must be made available for use through wetting of the pad. Upon wetting the pad, the pad dissolves and the dried cleansing compound is activated or released and made useful. These pads therefore require the presence of water to perform their cleansing function, and the pad itself is not particularly useful for cleaning.

There exists a need in the art for a dissolvable pad that provides a solution for delivery to a surface, wherein the solution does not have to be activated or released by water in order to be used, such that the pad itself can function as an applicator for the solution. Inasmuch as wipes and pads are provided for the delivery of other solutions, such as bug repellant compounds, sun screen compounds, surface treatment compounds and the like, there also exists a need in the art for a dissolvable pad that provides such other types of compounds for use, and is thereafter able to be safely disposed into public water systems.

SUMMARY OF THE INVENTION

This invention generally provides a dissolvable pad for delivery of a solution to a surface, the dissolvable pad comprising a water soluble substrate, and a solution retained in or on said water soluble substrate and available for use without activation by water.

The water soluble substrate is preferably composed of a starch-based material, and, in particular embodiments, is composed of a starch-based material derived from the group consisting of potato, wheat, corn, rice and other naturally derived plant matter. The water soluble substrate is soluble in water and biodegradable so as to be safely disposed of in public water systems by exposing it to water after the solution therein has been desirably employed. Because the solution in the water soluble substrate is available for use without exposing the substrate to water, the substrate may function as an applicator, and, in some embodiments, as a soft or abrasive scrubbing substrate as well.

The solution retained in the substrate may be any solution for surface treatment, including personal care, such as when the solution is to be applied to the "surface" of the body. Thus, many types of solutions are contemplated and covered herein, including personal cleansing compounds, sanitizing compounds, bug repellant compounds, sun screen compounds, and surface treatment compounds for treating inanimate surfaces. This list is to be understood as non-limiting on the scope of this invention, as other solutions appropriate for use in accordance with the invention may readily be known, discovered or created.

DESCRIPTION OF THE PREFERRED EMBODIMENTS

This invention provides a dissolvable pad for delivery of a solution to a surface. The dissolvable pad includes a water soluble substrate and a solution retained in or on said water soluble substrate. The term "pad" is to be understood to include any suitable substrate, whether or not it is considered to be a "pad" as that term in generally interpreted. Thus, tissue-like sheets or wipes, and more substantial three-dimensional shapes that might be specifically chosen for a given application, are to be included in scope of the term "pad."

The pad includes a "water soluble substrate," which is to be understood to refer a suitable substrate that is soluble in water, leaving no residual product. In preferred embodiments, the substrate is water soluble so as to be safely disposable into public water systems by exposing it to water after the solution therein has been desirably employed. A "suitable substrate" is one that can maintain its structural integrity while retaining the desired solution. The substrate is preferably biodegradable and environmentally safe. Additionally, the substrate is to retain the solution in a manner that makes the solution available for use without activation by water, i.e., the solution may be employed simply by rubbing the substrate onto the surface to which the solution is to be applied. The application of water is not necessary for releasing the solution from the pad. But in embodiments for applying a solution to skin from on or within the substrate, exposing the substrate to water, during use of the substrate, may be beneficial.

In one embodiment, the water soluble substrate is preferably composed of a starch-based material, and, in particular embodiments, is composed of a starch-based material. The starch-based material is preferably naturally derived from vegetable or other organic matter. In particular embodiments, the starch-based material is an extruded, starch-based material derived from plants selected from the group consisting of potato, wheat, corn, and rice. Such starch-based materials are now generally known, and may include those disclosed in U.S. Pat. Nos. 4,863,655, 5,266,368, and 6,054,204, the entirety of which are incorporated herein by reference. Known useful starch-based materials include Renature™ (STOROpack, Germany), ECO-FOAM™ (National Starch & Chemical, U.K.), FLO-PAK BIO 8™ (FP International, California, USA), and BioFoam™ (Johnson Corporation, USA). Starch is known to be beneficial to skin health, and is used in many cosmetics, and the use of starch-based substrates in accordance with this invention will be particularly beneficial in conjunction with skin care solutions, such as skin cleansing and sanitizing solutions.

In another embodiment, the water soluble substrate is a polyvinyl alcohol-based (PVA-based) material or other water soluble synthetic materials. Conventional grades of PVA are unaffected by animal and vegetable oils, greases, and petroleum hydrocarbons, making them desirable for use as substrates for the pads herein. Water soluble, environmentally friendly (i.e., safely disposable) PVA materials are generally known and are being employed currently in detergent applications, among others. Such PVA materials are typically provided as films formed into pouches to contain detergent therein. In popular applications, the detergent-containing pouch contains a unit dose of detergent, and is placed in washing machines or dishwashers (depending upon the type of detergent), where water dissolves the pouch to release the detergent for cleaning. Such PVA pouches are disclosed, by way of non-limiting example, in U.S. Pat. Nos. 4,844,828, 4,416,791, and 6,451,750. This invention, however, does not employ the pouch concept, and instead provides the PVA as a film substrate.

It has been found that PVA films can be developed to retain solution on their surface, thereby eliminating, for the applications focused upon herein, the need for forming a PVA pouch to hold solution. These PVA films are employed as the pad substrate herein. The surface tension of the solution is relied upon to retain the solution on a PVA film provided with nano-, micro-, and/or milli-scale surface area texture. The surface area can be textured in targeted areas to hold solution at particularly desired areas on the pad.

The solution retained in the water soluble substrate may be any solution for surface treatment, including hard surfaces and personal care, such as when the solution is to be applied to the "surface" of the body. The solution is retained in the water soluble substrate and is available for use without the need to use water to dissolve the substrate and/or release the solution. The substrate is water soluble so as to be readily and safely disposed in public and other water systems, and not for releasing the solution. Particularly, the substrate is safely disposed of in common sinks and drains, and will not cause clogging. The substrate is preferably chosen so that it does not pollute groundwater or compromise the functioning of common water systems. Because the solution in the water soluble substrate is available for use without exposing the substrate to water, the substrate may function as an applicator, and, in some embodiments, as a scrubbing substrate as well.

As a scrubbing substrate, the substrate allows one to focus a cleansing/scrubbing action on a particular soiled area. In the area of personal care, this is to be distinguished from current personal cleansing products in which a cleaning solution is taught to be spread across both soiled and unsoiled areas. In applications employing cleaning solutions for personal care, the starch-based substrate materials are preferably foam-like and provide micro-voids that function to gently scrub the skin to aid in cleansing. It will be appreciated that this scrubbing function is provided by the soluble substrate, such that rigid or semi-rigid abrasives, which have tended to clog domestic (and other) water systems, may not be necessary. However, in some applications, it might be desirable to include rigid or semi-rigid particles in the starch-based substrate, for a more aggressive scrubbing action.

For the PVA substrates, it has already been noted that the surface area is textured to aid in the retention of the solution through surface tension. This texture aids in scrubbing and cleaning in desired applications, and rigid and semi-rigid particles can be employed for more aggressive scrubbing.

Many types of solutions are contemplated and covered herein, including personal cleansing compounds, sanitizing compounds, bug repellant compounds, sun screen compounds, and surface treatment compounds for treating hard surfaces. This list is to be understood as non-limiting on the scope of this invention, as other solutions appropriate for use in accordance with invention may readily be known, discovered or created. The solutions are selected to be low in water content, as water may negatively impact the structural integrity of the substrate.

The solution is retained by the water soluble substrate by being impregnated or surface coated onto the substrate. In starch-based substrates according to this invention, the solution is preferably distributed throughout the substrate. Such impregnation is generally achieved with the starch-based substrates simply by allowing the substrates to absorb the solution, although the solution may alternatively be injected therein. As mentioned, for PVA substrates, the solution is surface coated onto the substrate, and surface tension and surface texture function to retain the solution on the substrate. Other methods that allow the solution to be available in the substrate may be employed.

Cleaning solutions for personal care are particularly desirable as the solution to be retained by the substrate. Any solution that does not compromise the substrate structure may be employed, and this will generally entail using a solution that has low water content, because high water contents would dissolve and compromise the substrate. The cleaning solution may consist of any of the following: aliphatic hydrocarbons, terpene hydrocarbons (e.g., d-limonene), alcohols, polyols, dibasic esters, vegetable oils, esters of vegetable oils, silicon oils, acetates, lactates, n-methyl pyrrolidones, carbonate solvents, oxidizing agents (e.g., peroxide), and detergents, such as non-ionic, cationic, and anionic types. Agents can also be added for antimicrobial and/or antiviral effects. Various other additives, dyes, and fragrances may be included.

In one embodiment, cleaning solutions may include from 0 to 100% by weight of compounds selected from the group consisting of aliphatic hydrocarbons, terpene hydrocarbons, alcohols, polyols, dibasic esters, vegetable oils, esters of vegetable oils, silicon oils, acetates, lactates, n-methyl pyrrolidones, carbonate solvents, oxidizing agents and combinations thereof; from 0 to 100% by weight detergents; from 0 to 5% by weight water; and from 0 to 15% by weight of other common additives, including antimicrobials, colorants, fragrances, moisturizers, and the like.

In accordance with this invention, particularly preferred cleaning solutions may include from about 10 to 90% by weight of compounds selected from the group consisting of aliphatic hydrocarbons, terpene hydrocarbons, alcohols, polyols, dibasic esters, vegetable oils, esters of vegetable oils, silicon oils, acetates, lactates, n-methyl pyrrolidones, carbonate solvents, oxidizing agents, and combinations thereof; from about 0 to about 10% by weight detergents; from about 0 to about 2% by weight water, and from about 0.05 to about 15% by weight of the group selected from antimicrobials, colorants, fragrances, moisturizers, and combinations thereof.

A first particularly preferred cleaning solution includes from about 75 to about 100% by weight of a soy ester, from about 0 to about 10% by weight of a non-ionic detergent, from about 0 to about 15% by weight additives.

In a starch-based substrate embodiment employing cleaning solutions, the dissolvable pad is preferably comprised of from 5 to 95% by weight of the substrate, and from 95 to 5% by weight of the cleaning solution. In accordance with one embodiment, the substrate makes up 30 to 95 wt. % of the dissolvable pad, and the cleaning solution makes up 70 to 5 wt. % of the dissolvable pad. In accordance with another embodiment, the substrate makes up 70 to 95 wt. % of the dissolvable pad, and the cleaning solution makes up 30 to 5 wt. % of the dissolvable pad. In the starch-based embodiments, the water content is preferably kept below 5%, more preferably 2%, and, most preferably 1% by weight.

In the PVA substrate embodiments employing cleaning solutions, the dissolvable pad is preferably comprised of from 70 to 99.5% by weight of the substrate, and from 30 to 0.5% by weight of the cleaning solution. In accordance with one embodiment, the substrate makes up 80 to 99 wt. % of the dissolvable pad, and the cleaning solution makes up 20 to 1 wt. % of the dissolvable pad. In accordance with another embodiment, the substrate makes up 90 to 99 wt. % of the dissolvable pad, and the cleaning solution makes up 10 to 1 wt. % of the dissolvable pad. In the PVA embodiments, the water content is preferably kept below 10%, more preferably 2%, and, most preferably 1% by weight.

Sanitizing solutions for personal use are also particularly preferred solutions. The sanitizing solution may consist of various alcohols, including, but not limited to, ethanol, propanol, isopropanol, and butanol. The sanitizing solution preferably includes from about 70 to 100% by weight alcohol; from 0 to 30% by weight water, and from 0 to 15% by weight of other additives, including antimicrobials, colorants, fragrance, moisturizers, and the like. It will be appreciated that higher levels of water may be present in alcohol-based sanitizers without compromising the substrate.

Particularly useful sanitizing solutions include those disclosed in U.S. Pat. No. 6,333,039, and U.S. Pending application Ser. No. 10/068,622, all of which are incorporated herein by reference. It should be appreciated that the carbomers and related gelling agents (either natural or synthetic) need not be employed.

In starch-based substrate embodiments employing sanitizing solutions, the dissolvable pad is preferably comprised of from 50 to 95% by weight of the substrate, and from 50 to 5% by weight of the sanitizing solution. In accordance with one embodiment, the substrate makes up 70 to 95 wt. % of the dissolvable pad, and the sanitizing solution makes up 30 to 5 wt. % of the dissolvable pad. In accordance with another embodiment, the substrate makes up 80 to 95 wt. % of the dissolvable pad, and the sanitizing solution makes up 20 to 5 wt. % of the dissolvable pad.

EXPERIMENTAL

Renature™ (STOROpack, Germany) loosefill "peanuts" were employed as the substrate. This loosefill was placed in a container holding a cleaning solution, and the solution was absorbed into the substrate to provide a dissolvable cleaning pad. The cleaning solution had the following ingredients:

| | |
|---|---|
| soy ester | 82.8% by weight |
| ethoxylated fatty alcohol (Plurafac D25, BASF, USA) | 5.7% by weight |
| additives | 11.5% by weight. |

Typically, the substrate was around 0.15 g, and retained about 0.75 to 0.85 g of solution.

Tests were run to qualitatively analyze how effective the dissolvable cleaning pads were in cleaning hands. A test subject's hand was soiled with different material, as listed below, and the removal of the material was rated on a scale of from 1 to 5. In removing the material, the cleaning pad was rubbed against the soiled area of the test subject's hand until a visible lifting of the material was evident, and then further rubbing continued to remove the material. No water was used while the pad was rubbed against the soiled area, and the cleaning solution was yet able to affect the soiled area.

Once the material appeared to be lifted from the hand, the test subject rinsed the entire cleaning pad and their hands under water in a typical washing motion. The pad then dissolved away and rinsed down the drain. The following table provides a qualitative analysis of material removal.

| Material removed | Removal rating (1 = poor, 5 = excellent) |
|---|---|
| Tar | 5 |
| Oil/Carbon black dirt simulate | 5 |
| Ink | 3 |
| Paint primer | 5 |

It is noted that while the ink removal was not rated very high, this is a result of the cleaning solution employed, and a different cleaning solution could be employed in the substrate to target ink removal. Indeed, it is envisioned that different cleaning pads could be offered with different cleaning solutions targeting the removal of different materials. And the solution in/on the substrate need not be a cleaning solution.

In light of the forgoing, it can be seen that this invention provides an improvement in the application of solutions to surfaces. While a full and complete description of the invention has been set forth in accordance with the dictates of the Patent Statutes, it should be understood that modifications can be resorted to without departing from the spirit hereof or the scope of the appended claims.

What is claimed is:

1. A dissolvable pad for delivery of a solution to a surface, the dissolvable pad comprising:
    a water-soluble substrate selected from a water-soluble starch-based material and a polyvinyl alcohol material; and
    a solution impregnating or surface coated on said water-soluble substrate and released therefrom upon pressing and rubbing said water-soluble substrate against a surface such that the solution is delivered and rubbed onto the surface, said solution being released from the substrate without contacting the substrate with water.

2. The dissolvable pad of claim 1, wherein the starch of the starch-based material is derived from the group consisting of potato, corn, wheat and rice.

3. The dissolvable pad of claim 1, wherein said water-soluble substrate is a water-soluble starch-based material and said solution is retained in said water-soluble substrate by being impregnated therein.

4. The dissolvable pad of claim 3, wherein said solution is impregnated in said water-soluble substrate by being absorbed or injected therein.

5. The dissolvable pad of claim 1, wherein said water-soluble substrate is a polyvinyl alcohol material and said solution is retained on said water-soluble substrate by being surface coated thereon.

6. The dissolvable pad of claim 5, wherein said solution is surface coated onto said water-soluble substrate by being sprayed thereon.

7. The dissolvable pad of claim 1, wherein said water-soluble substrate is abrasive.

8. The dissolvable pad of claim 1, wherein said solution is selected from the group consisting of personal care cleaning compounds, surface cleaning compounds, bug repellant compounds, and sun screen compounds.

9. The dissolvable pad of claim 1, wherein said water soluble substrate is safely disposable in public and other water systems, and does not pollute ground water.

10. A dissolvable pad for delivery of a solution to a surface, the dissolvable pad comprising:
    a foam-like water-soluble substrate made of an extruded starch-based material and including micro-voids; and
    a solution selected from a cleaning solution and a sanitizing solution, said solution being retained in said water-soluble substrate such that said cleaning solution can be applied to a surface by rubbing the water-soluble substrate against said surface, wherein said micro-voids serve to scrub said surface and the application of water is not necessary for releasing the cleaning solution from said water-soluble substrate.

11. The dissolvable pad of claim 1, wherein said solution is a cleaning solution for personal care comprising:
from 10 to 90% by weight of compounds selected from the group consisting of aliphatic hydrocarbons, terpene hydrocarbons, alcohols, polyols, dibasic esters, vegetable oils, esters of vegetable oils, silicon oils, acetates, lactates, n-methyl pyrrolidones, carbonate solvents, oxidizing agents, and combinations thereof,
from 0 to about 10% by weight detergents,
from 0 to about 2% by weight water, and
from 0.05 to about 15% by weight of the group selected from antimicrobials, colorants, fragrances, moisturizers, and combinations thereof.

12. The dissolvable pad of claim 1, wherein said solution is a sanitizing solution comprising:
from 70 to 100% by weight alcohol,
from 0 to 30% by weight water, and
from 0 to 15% by weight of additives selected from the group consisting of antimicrobials, colorants, fragrance, moisturizers, and the like.

* * * * *